(12) United States Patent
Besson

(10) Patent No.: US 6,463,118 B2
(45) Date of Patent: Oct. 8, 2002

(54) COMPUTED TOMOGRAPHY (CT) WEIGHTING FOR HIGH QUALITY IMAGE RECONTRUCTION

(75) Inventor: Guy M. Besson, Broomfield, CO (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 25 days.

(21) Appl. No.: 09/751,074

(22) Filed: Dec. 29, 2000

(65) Prior Publication Data
US 2002/0122528 A1 Sep. 5, 2002

(51) Int. Cl.[7] .................................................. A61B 6/03
(52) U.S. Cl. .......................................... 378/15; 378/901
(58) Field of Search ............................... 378/4, 15, 901

(56) References Cited

U.S. PATENT DOCUMENTS

| | | |
|---|---|---|
| 5,559,847 A | 9/1996 | Hu et al. |
| 5,606,585 A | 2/1997 | Hu |
| 5,818,896 A | 10/1998 | Hsieh |
| 5,960,056 A | 9/1999 | Lai |
| 5,991,356 A | 11/1999 | Horiuchi et al. |
| 6,233,308 B1 | 5/2001 | Hsieh |
| 6,269,139 B1 | 7/2001 | Hsieh |
| 6,285,732 B1 | 9/2001 | Hsieh |
| 6,301,325 B1 | 10/2001 | Besson et al. |
| 6,324,247 B1 * | 11/2001 | Besson .......................... 378/15 |
| 6,339,632 B1 * | 1/2002 | Besson .......................... 378/15 |
| 6,351,514 B1 * | 2/2002 | Besson .......................... 378/15 |

* cited by examiner

Primary Examiner—David V. Bruce
(74) Attorney, Agent, or Firm—Carl B. Horton, Esq.; Armstrong Teasdale LLP

(57) ABSTRACT

One aspect of the present invention is a CT imaging method. An object is scanned at a selected helical pitch to acquire a set of attenuation measurement. For each angle of a fan beam of radiation, a direct and a conjugate set of attenuation measurements are identified that each include at least two measurements closest to a plane of reconstruction. Measurements are arranged in pairs, including a short pair and a long pair, using direct and conjugate measurements. Direct measurements are weighted in accordance with their distance from the plane of reconstruction. Direct measurements of the short and long pairs are blended according to a blending function that weights the short pair contribution to zero at a point at which the selected direct pair and the selected conjugate pair have a same z-axis location. The weighted and blended data is used to reconstruct an image of the object.

18 Claims, 9 Drawing Sheets

Row-Extrapolation condition for row 8, Row-Interpolation condition for row 1.

Row-Extrapolation condition for row 1, Row-Interpolation condition for row 8.

COMPUTED TOMOGRAPHY (CT) WEIGHTING FOR HIGH QUALITY IMAGE RECONTRUCTION

BACKGROUND OF THE INVENTION

This invention relates generally to methods and apparatus for reconstruction of computed tomographic image and more particularly to methods and apparatus for weighting of data to improve the quality of such reconstructed images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsffield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

The x-ray beam is projected from the x-ray source through a pre-patient collimator that defines the x-ray beam profile in the patient axis, or z-axis. The collimator typically includes x-ray-absorbing material with an aperture therein for restricting the x-ray beam. In at least one known CT imaging system, a scanning mode and corresponding reconstruction method are implemented for 3:1 and 6:1 helical pitches. The 6:1 helical pitch mode is referred to as a "high speed" mode because volume coverage is large, and scanning is faster along z-axis than in the 3:1 helical pitch mode. However, the scanning and reconstruction techniques used for this high speed mode have not been found suitable for scanning at greater helical pitches, for example, 8:1 or higher. One of several reasons that these techniques have not been found suitable is that the 6:1 high speed mode uses conjugate sampling pairs that are, in general, no longer valid at pitches of 8:1 or more.

It would be desirable to provide methods and apparatus that provide the thinnest slice sensitivity profile available from acquired data at a fairly high pitch, without deconvolution. It would further be desirable to provide methods and apparatus that can be applied to CT imaging systems with various numbers of detector rows, and at multiple pitches

BRIEF SUMMARY OF THE INVENTION

One aspect of the present invention is a CT imaging method. An object is scanned at a selected helical pitch to acquire a set of attenuation measurement. For each angle of a fan beam of radiation, a direct and a conjugate set of attenuation measurements are identified that each include at least two measurements closest to a plane of reconstruction. Measurements are arranged in pairs, including a short pair and a long pair, using direct and conjugate measurements. Direct measurements are weighted in accordance with their distance from the plane of reconstruction. Direct measurements of the short and long pairs are blended according to a blending function that weights the short pair contribution to zero at a point at which the selected direct pair and the selected conjugate pair have a same z-axis location. The weighted and blended data is used to reconstruct an image of the object.

It will be seen that the various embodiments of the present invention provide thin slice sensitivity profiles from acquired data at a fairly high pitch, without deconvolution. Moreover, the methods and apparatus embodiments of the present invention can be applied to CT imaging systems with various numbers of detector rows, and at multiple pitches.

embodiments of the invention take into account conjugate measurements for interpolation and extrapolation.

Figure 8:
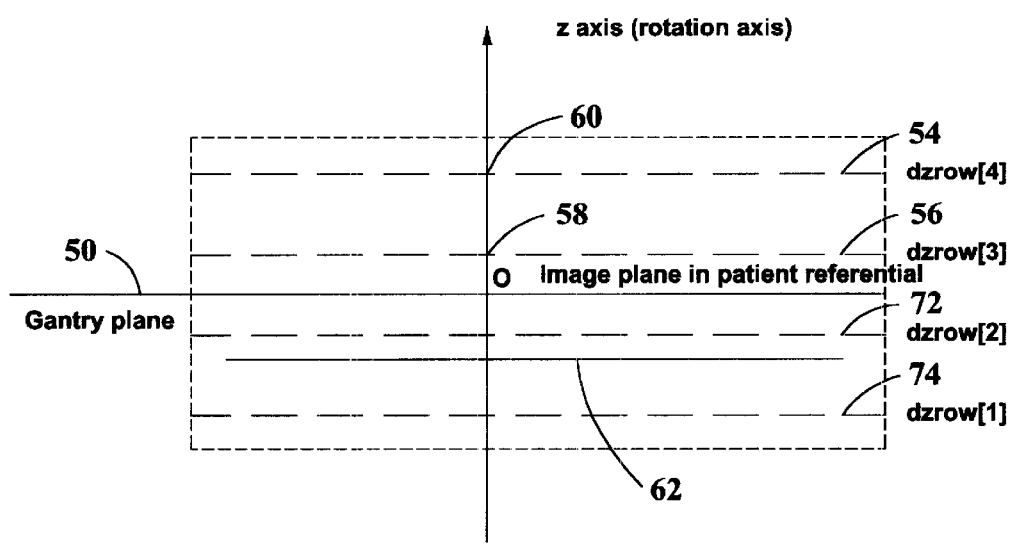

FIG. 8 is a representation of a row-interpolation condition. This should not be interpreted as meaning that row extrapolation necessarily occurs; embodiments of the invention take into account conjugate measurements for interpolation and extrapolation.

Figure 9:
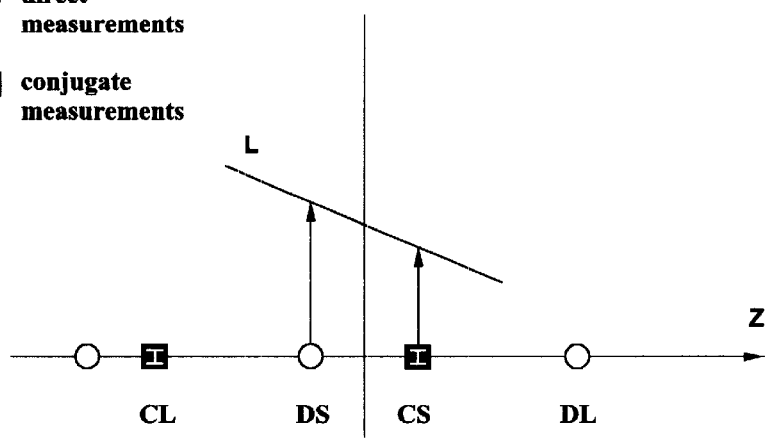

FIG. 9 is a representation of four measurements closest to a plane of reconstruction, for a given line integral.

Figure 10:
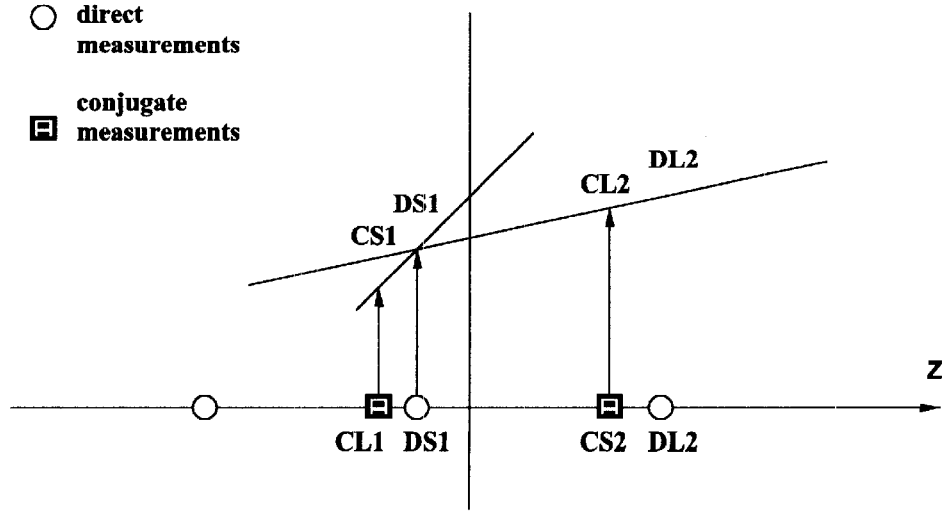

FIG. 10 is a representation of four measurements closest to a plane of reconstruction, for a given line integral and a case in which a pair of measurements are on the same side of a plane of reconstruction.

Figure 11:
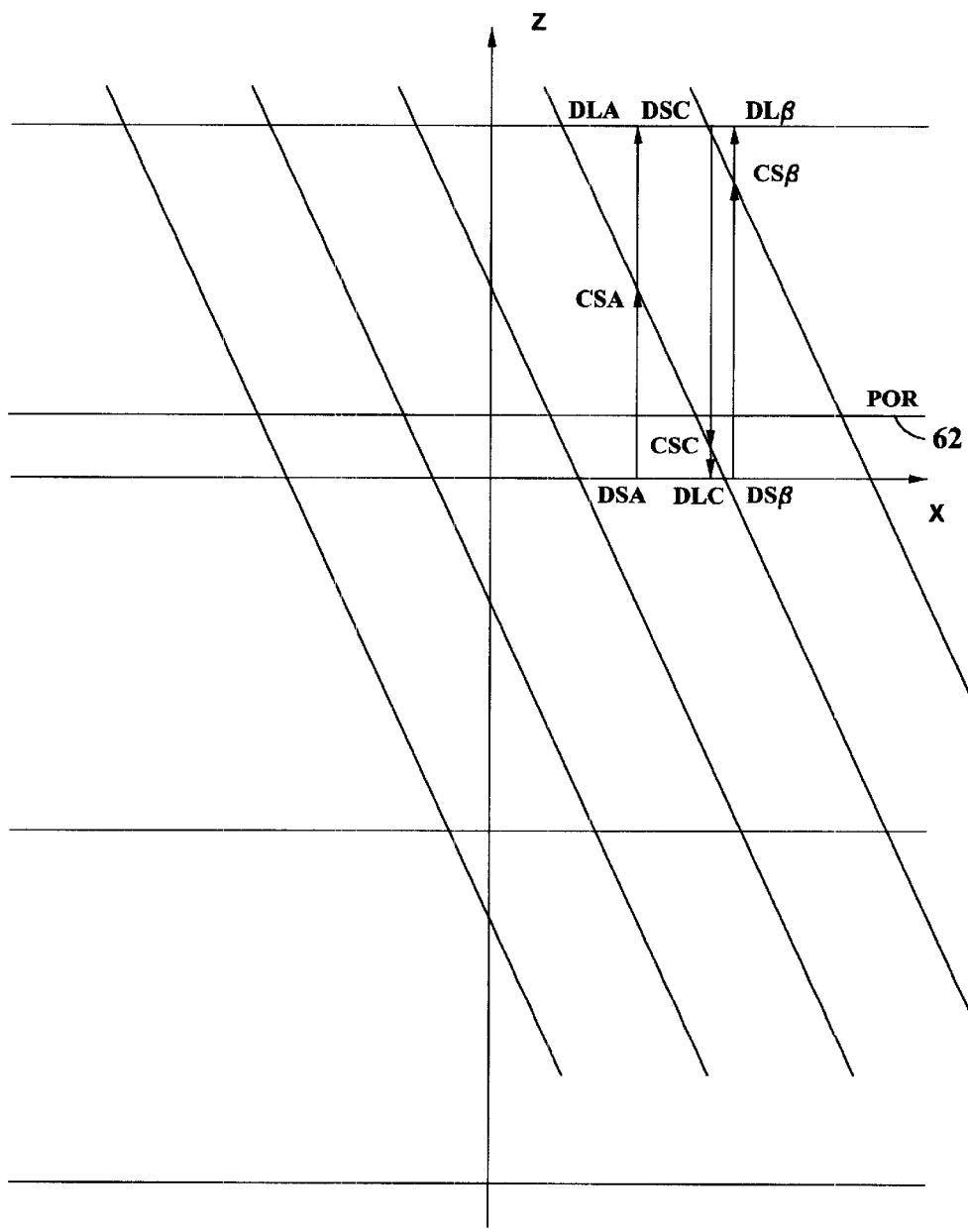

FIG. 11 is a representation of three pair selection conditions that occur in one embodiment of the present invention at pitches less than 7:1.

Figure 12:
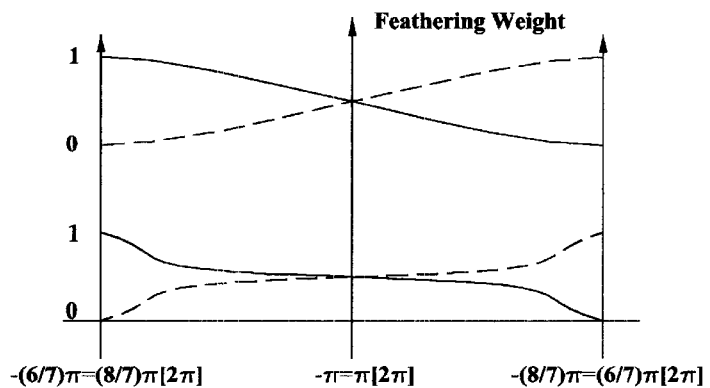

FIG. 12 is a representation of feathered weights.

Figure 13:
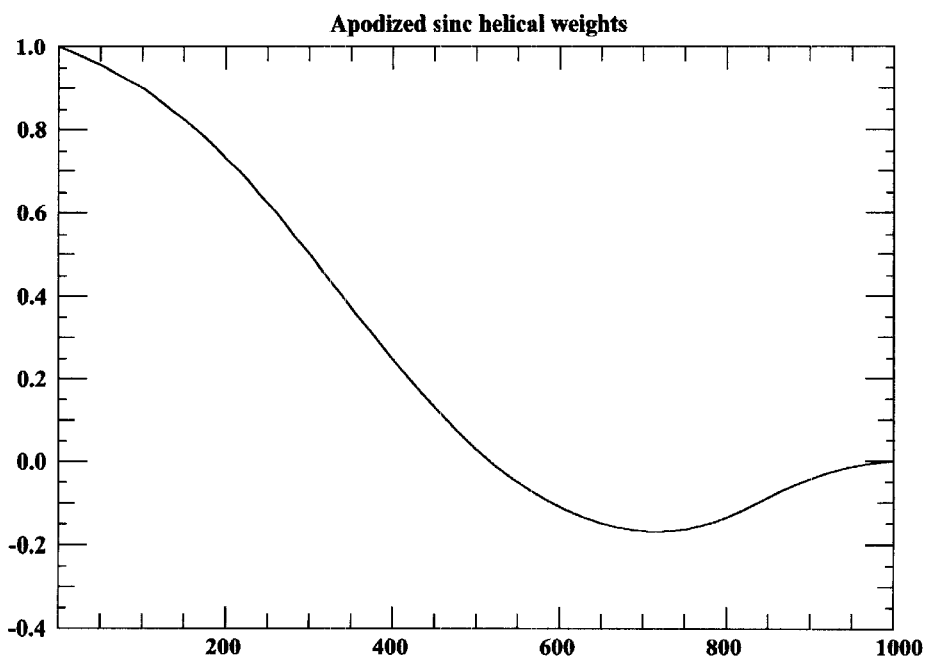

FIG. 13 is a representation of an Apodized sinc( ) weighting function.

Figure 14:
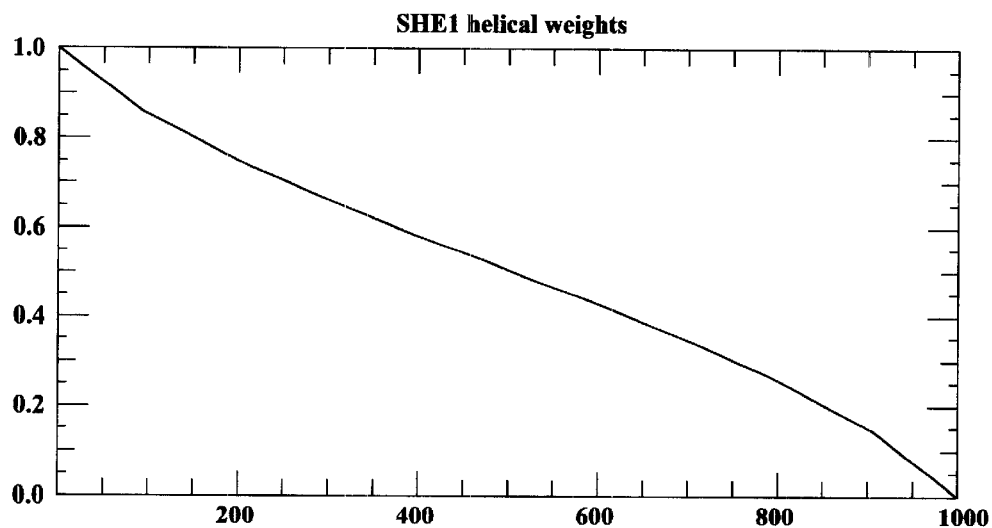

FIG. 14 is a representation of a SHE1 helical weighting function.

Figure 15:
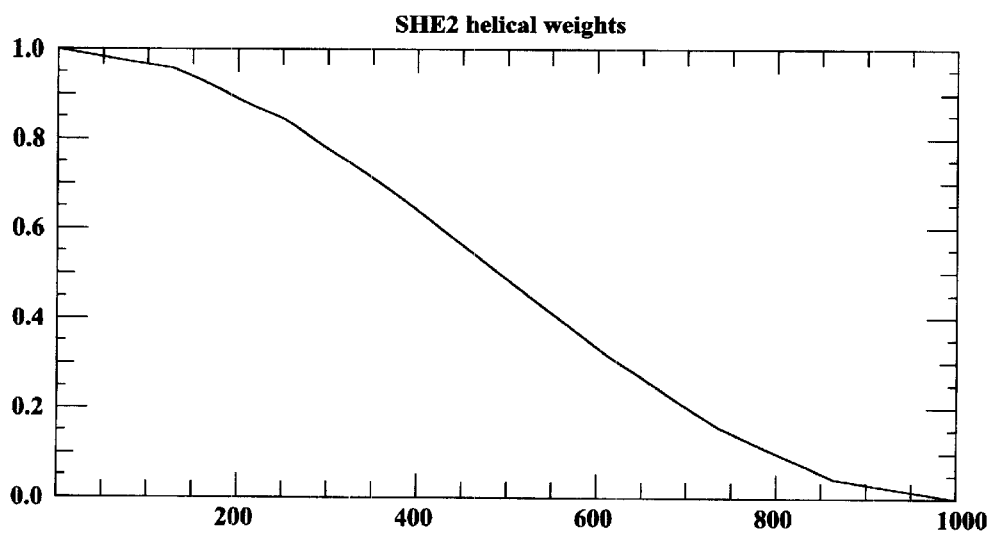

FIG. 15 is a representation of a SHE2 helical weighting function.

DETAILED DESCRIPTION OF THE INVENTION

Figure 1:
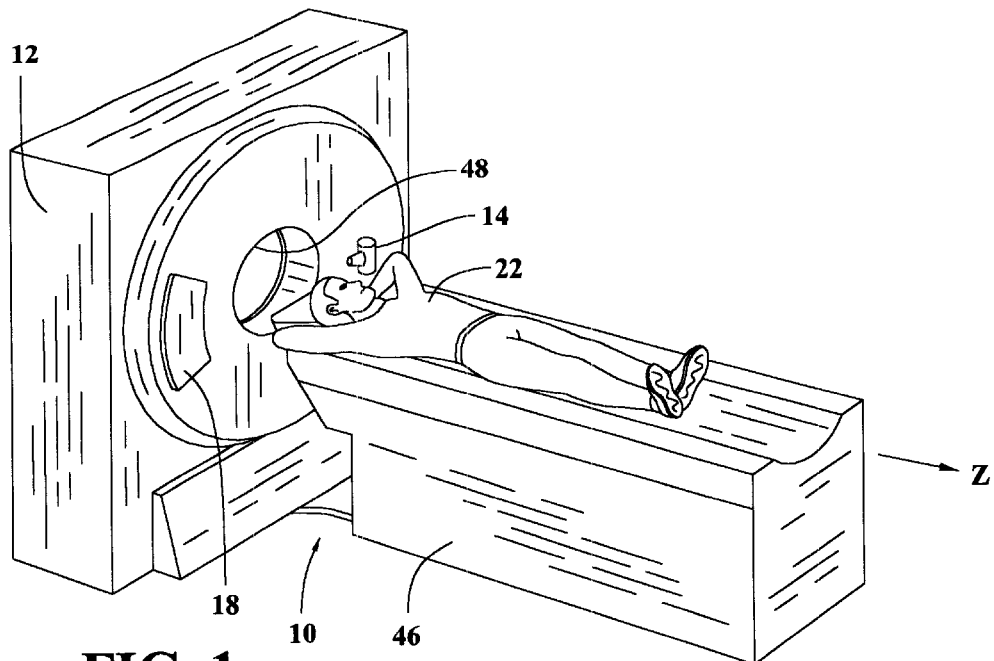
FIG. 1 is a pictorial view of a CT imaging system.
Figure 2:
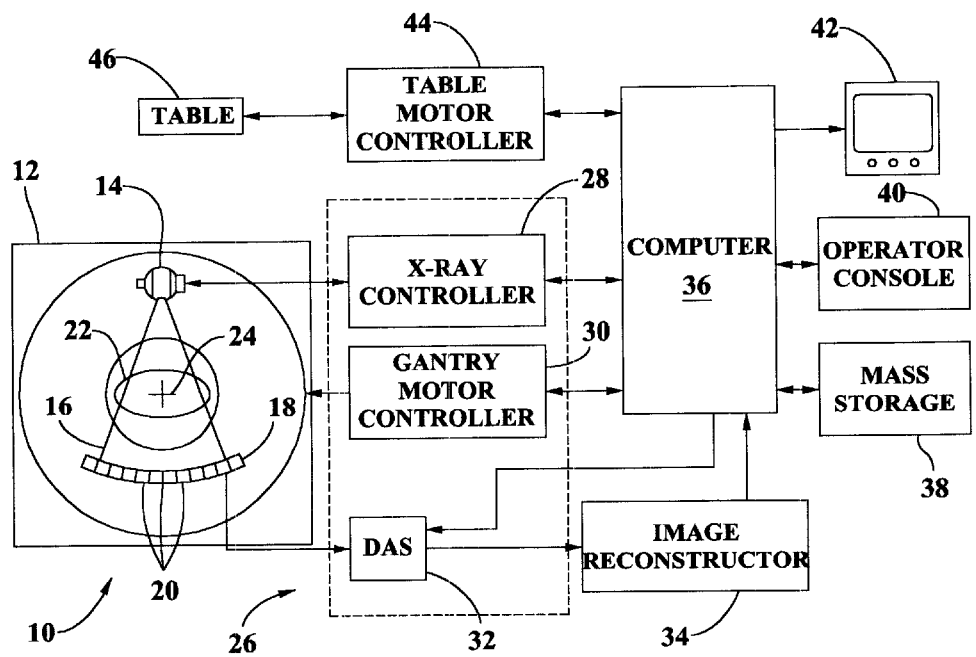
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam. As the x-ray beam passes through a patient 22, the bean is attenuated. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
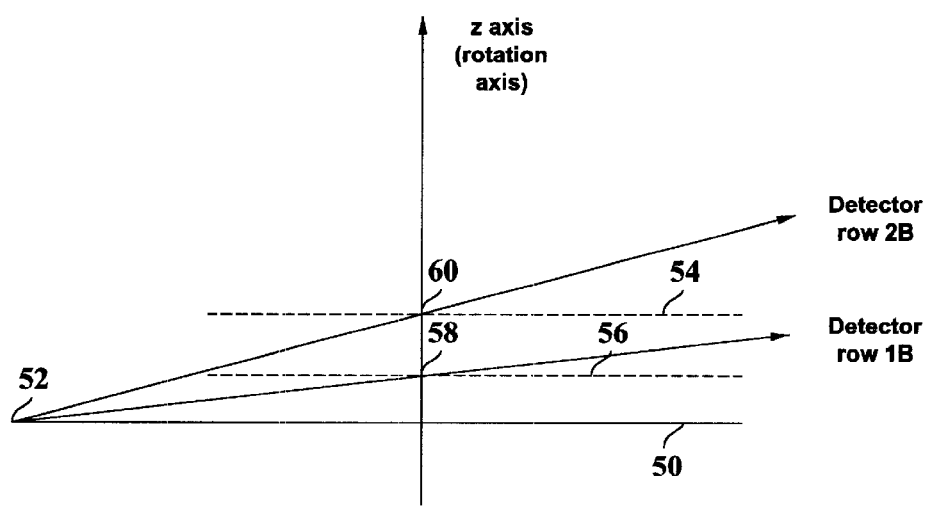
FIG. 3 is a representation of a multislice cone-beam geometry shown for a "B"-side of a 4-slice CT imaging system. Cone angles are greatly exaggerated in this illustration.

Referring to FIG. 3, gantry plane 50 is defined as a plane orthogonal to the z-axis and passing through a center of focal spot 52 of x-ray source 14. Gantry plane 50 exactly bisects detector array 18 in the z-axis. Also, gantry plane 50 passes between detector array 18 rows (also known as macro-rows) conventionally labeled 1A and 1B. (Rows are numbered consecutively from gantry plane 50, with a letter "A" or "B" appended to identify which side of gantry plane 50 the row is on. In FIG. 3, only rows 1B and 2B are represented.) In FIG. 3, planes 54 and 56 are planes associated with centers of detector row 2B and 1B, respectively.

Because a 2D backprojection is used, all fan-rays of x-ray beam 16 measured by a detector array 18 macro-row (e.g., 1B, 2B) for a given source 14 position are assumed to be coplanar, in a plane (e.g., 54, 56) orthogonal to z. Its distance to gantry plane 50 uniquely characterizes this associated plane. That distance in turn depends on an aperture selected (on the 4 slice system, 4×5 mm, 4×3.75 mm, 4×2.5 mm, 4×1.25 mm). Planes 56 and 54 intersects the z-axis (at 58, 60, respectively) where the z-axis center of the associated detector array 18 macro-row projects.

At least one known CT imaging system embodiment includes one or more programs that rely on a 2D (i.e., two-dimensional) backprojection. Accordingly, cone-angles of individual line integrals are ignored and all rays acquired at a given source 14 position and by a given detector array 18 row (e.g., 1B or 2B) are described as belonging to a single plane (e.g., 54, 56) orthogonal to the z-axis. This plane is uniquely described by its z-distance to the gantry plane.

Figure 4:
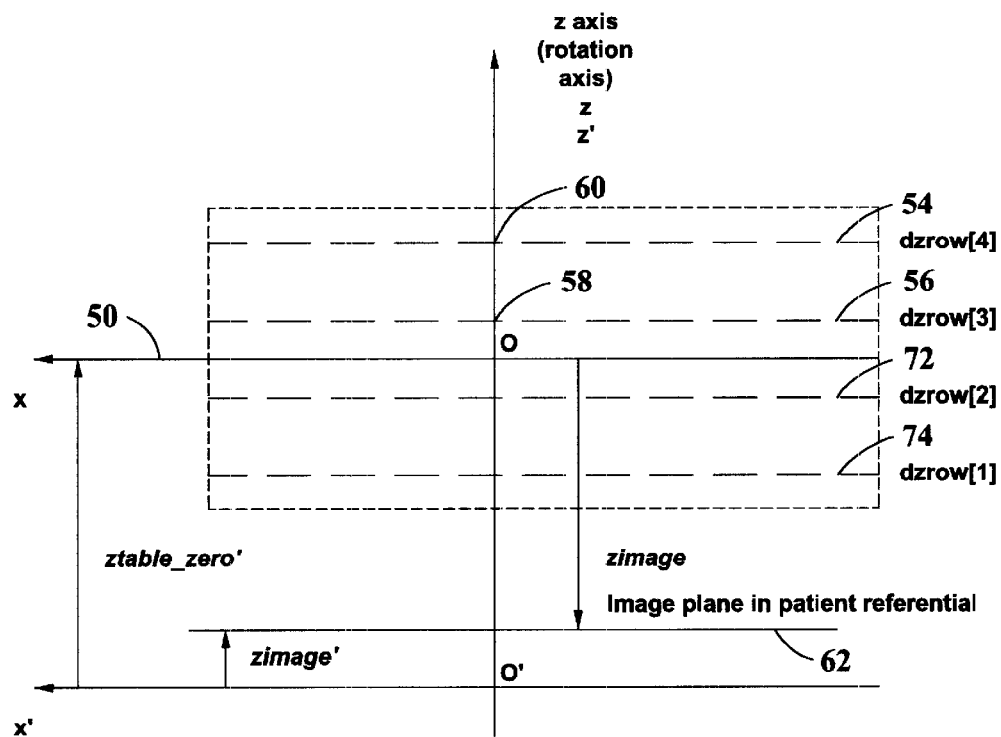
FIG. 4 is a graph showing representations of a patient referential translated with respect to a gantry referential.

FIG. 4 is a representation of two coordinate systems O, x, y, z and O',x',y',z' relevant to helical scanning calculations. A first coordinate system or gantry referential O, x, y, z is associated with gantry 12 in such a way that gantry plane 50 passes through O and contains axes x and y. A second coordinate system or patient referential O',x',y',z' is translated from first referential O, x, y, z and associated with patient table 46. The coordinate of gantry plane 50 at time=0 in patient referential O',x',y',z' is denoted by ztable_zero'. The coordinate of a reconstructed image plane 60 in patient referential O',x',y',z' is denoted by zimage'. Each detector 18 row (as projected on isocenter 24, as in FIG. 1) has an associated z-coordinate dzrow[i] in gantry coordinate system O, x, y, z; i=1, . . . , Number_of_rows. For example, for a four slice system 10 at 4×5 mm, dzrow[1]=−7.5 mm, dzrow[2]=−2.5 mm, dzrow[3]=+2.5 mm, dzrow[4]=+7.5 mm. For an eight slice system 10 at 8×2.5 mm, dzrow[1]=−8.75 mm, dzrow[2]=−6.25 mm, dzrow[3]=−3.75 mm, dzrow[4]=−1.25 mm, dzrow[5]=+1.25 mm, dzrow[6]=+3.75 mm, dzrow[7]=+6.25 mm, and dzrow[8]=+8.75 mm.

Zimage is written:

$$zimage = -(ztable\_zero' - (iview-1) \times dzview - zimage')$$

where iview is a view index (equal to 1 at time=0), and dzview is a z-increment between two views.

In a HQ (high quality) image reconstruction mode, a pitch of 7:1 for in one embodiment of imaging system 10 provides both optimal worst cone angle effect abatement and conjugate ray interlacing. In one embodiment, and in such a scanning mode, 8/7ths of a full rotation is required for reconstruction plane 62 to cross the width of detector array 18 from one edge to the other. This embodiment allows for half a macro-row extrapolation, or exactly one full rotation from a center of row 1 to a center of row 8. To obtain cone-beam artifact abatement, overscan weighting is used in one embodiment so that 8/7 (or more) of a source rotation will contribute to a given image plane 62.

In one embodiment, helical weighting is performed according to a general distance function calculation. A simple linear interpolation/extrapolation may be implemented. To eliminate the weight derivative discontinuities that occur with linear interpolation/extrapolation, a known generalized distance function approach can be used to smooth transitions from row-to-row.

In known multislice CT imaging systems 10, either four or eight samples are available at each projection. To provide more accurate interpolation/extrapolation, it is desirable to perform higher order calculations from the multiple available samples from each projection. Although such higher order calculations can be implemented readily on an image quality test bed, data flow changes make it difficult to practically incorporate such calculations into image generator boards of imaging systems 10.

Accordingly, in one embodiment of the present invention, a higher order interpolation is performed without non-linear calculations in the data itself (although non-linear weights are used in one embodiment). Weights are derived from a modified general interpolation function, for example, an apodized version of a sinc( ) function as used in Shannon-Whittier interpolation.

In one embodiment, when only two points for interpolation/extrapolation are used, a specific generalized distance function is derived such that i) the sum of the weights for the two samples is 1.0; and ii) the weight function does not present derivative discontinuities.

When using more than 2 points, such as in embodoiments using the apodized-sinc function, the weight sum is normalized to 1.0. This constraint is not explicitly taken into account when designing the generalized weight function. Normalization is done, for example, by calculating weights associated with each row contributing to a given estimate and dividing each weight contribution by the sum of the weights.

In one embodiment utilizing multislice scanning, two measurements of a single ray in a plane of reconstruction (POR) 62 are along rays at different angles through patient 22 with respect to POR 62. This is due to the cone-beam effect on data acquired on a multislice system 10. Overscan weights are used to handle resulting data discontinuities that occur at a 0, $2\pi$ interface even in the absence of motion of patient 22. Extrapolation of projection data in z over half the extent of a macro-row results in at least ($8/7$)×$2\pi$ worth of super-views contributing to a given image plane reconstruction. The amount over 360 degrees enables the application of the overscan weights, and blending of cone-angle discontinuities that occur at the 0, $2\pi$ interface. In another embodiment, as an alternative to extrapolation, projection data acquired $2\pi$ away (in source angle) is used for interpolation.

Overscan weights in one embodiment are written:

$$f(x) = 3x^2 - 2x^3,$$

where x varies between 0 and 1 in the interval considered. In another embodiment, overscan weights are written:

$$f(x) = \frac{\left|\sin(\frac{\pi}{2}(1+x))\right|^\delta}{\left|\cos[\frac{\pi}{2}(1+x)]\right|^\delta + \left|\sin[\frac{\pi}{2}(1+x)]\right|^\delta},$$

where x varies between 0 and 1 in an interval considered, and $\delta$ is a parameter.

To reconstruct a specific image plane 62 in patient 22, a "center view" is identified. The center view is a view that is within POR 62 or that is closest, in z, to the z-coordinate of POR 62. A range of super-views to be accessed and helical weights over that range are determined. Helical weights for a given row and a given source position are determined in one embodiment by a function call, which, in one exemplary embodiment, is written:

weight=hw_func(zrow−zimage,case,func_type,hw_mode).

In this function call, case specifies interpolation or extrapolation; func_type is an index into a generalized distance function; and hw_mode indicates whether interpolation or extrapolation is used. Helical weights are normalized, so that the total for all rows contributing to an image plane 62 is 1.0.

In some embodiments, z-smoothing is applied. In these embodiments, a loop over a number of images summed (i.e., a number of z-smoothing kernel points) is used to determine final weights.

In one exemplary embodiment of multislice scanner 10, N rows (N slices) of projection data are acquired for each view angle. A definition for a helical pitch p at which the data are acquired is written:

$$p = \frac{\text{Table\_Advance\_per\_rotation}}{\text{Slice\_width\_at\_isocenter}} = \frac{\Delta Zr}{\Delta z}.$$

In one exemplary embodiment in which p<N:1, for a given ray of x-ray in an image plane 62, two or more samples are acquired. The relatively slow pitches in this embodiment lead t o increased sampling as well as trade-offs between IQ, noise, patient motion, and temporal resolution.

In another exemplary embodiment in which p=N:1, for a given ray in an image plane 62, two samples are obtained for two different source 14 positions, allowing mA current reduction for x-ray source 14 and providing at least two samples for helical weighting reconstruction.

In another exemplary embodiment in which N:1<p<2N:1, some rays are sampled twice, while others are only sampled at one source 14 position. For rays sampled at only one source position, helical weighting is done using row-to-row interpolation, as in "segment reconstruction" (i.e., "half scan reconstruction"). In another embodiment, as an alternative to the use of partial scan reconstruction, overscan with interpolation is used.

In embodiments in which p>2N:1, some rays are sampled once, while others are not directly sampled. Accordingly, image quality is degraded relative to other embodiments.

In embodiments in which true cone-correction is not done in the backprojection, cone-artifact abatement is achieved using a combination of optimized pitch and helical weights. An optimum pitch for an N slice scanner 10 to reduce a cone-beam artifact associated with detector array 18 row number C (counted from gantry plane 50) is 2C-1. The row (or slice) aperture at isocenter is $\Delta z$.

Figure 5:
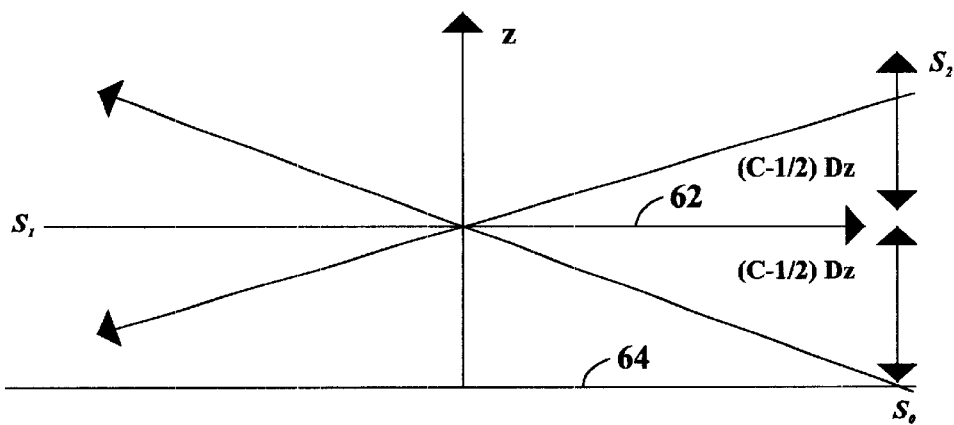
FIG. 5 is a representation of optimal pitch angles that are used in one embodiment to reduce cone-beam artifacts associated with a slice number C of a multislice scanner.

Referring to FIG. 5, optimal pitch is used in one embodiment to reduce cone-beam artifacts associated with slice number C of a multirow scanner 10. For a source 14 position S0, an image reconstruction plane 62 having a worst cone-angle is at an offset (C-1/2)Dz from a plane 64 orthogonal to the z axis associated with source position S0 . After a 180 degree rotation, a source 14 at position S1 is exactly in plane of reconstruction 62. After another 180 degrees rotation, source 14 is at a position S2 with a cone angle through reconstruction plane 62 exactly opposite that of source position $S_0$.

Thus, three measurements are collected for an image plane 62 corresponding to row C at a given source position S0. As S0 and S2 are acquired with opposite cone-angles, their associated artifacts average out. S1 is acquired in a plane and therefore without cone-angle error. (In embodiments in which imaging system 10 has an even number of rows in detector array 18, S1 is acquired as an average of two adjacent row readings) Accordingly, for an N slice imaging system 10 with N=2N', a worst-case cone-angle is associated with the outer slices and the best helical pitch for cone-angle artifact abatement is 2N'-1=N-1.

Figure 6:
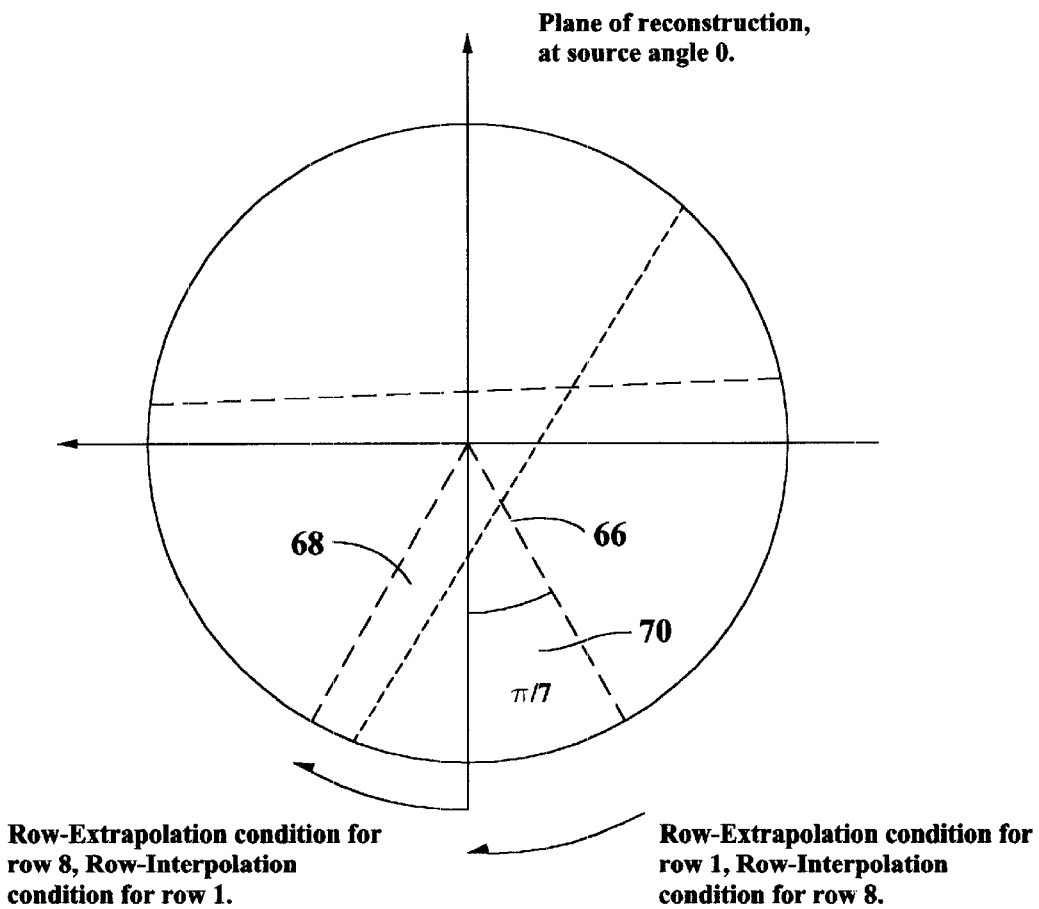
FIG. 6 is a representation of a range of source positions contributing to reconstruction of an image.

Referring to FIG. 6, to describe a range of source positions contributing to the reconstruction of a given image, let us assume that a center view is at a twelve o'clock position (source angle β=0). A range 66 of source angle overlap is indicated near the 6 o'clock position in FIG. 6 for a case RowO=0.0, where RowO a the parameter describing an amount of overlap used in helical weighting for cone-beam artifact abatement. For an embodiment having eight detector 18 rows, source angle overlap range 66 includes a first range 68 having a row-extrapolation condition for row 1 and a row-interpolation condition for row 8. Source angle overlap range 66 also includes a second range 70 having a row-extrapolation condition for row 8 and a row-interpolation condition for row 1.

In one embodiment, a weighting is used that includes source positions starting from the first contributing view to the last. Using the convention of FIG. 6 (i.e., assuming reconstruction plane 62 to be at a source angle β=0, i.e., a 12 o'clock position, which also defines a center view, at an origin of contributing view angles), and further assuming table 46 to be moving into gantry opening 48 of imaging system 10 from a table anchor position, contributing data are acquired with source positions written as:

$$((8+\text{RowO})/7)\pi <= \beta <= ((8+\text{RowO})/7)\pi.$$

Figure 7:
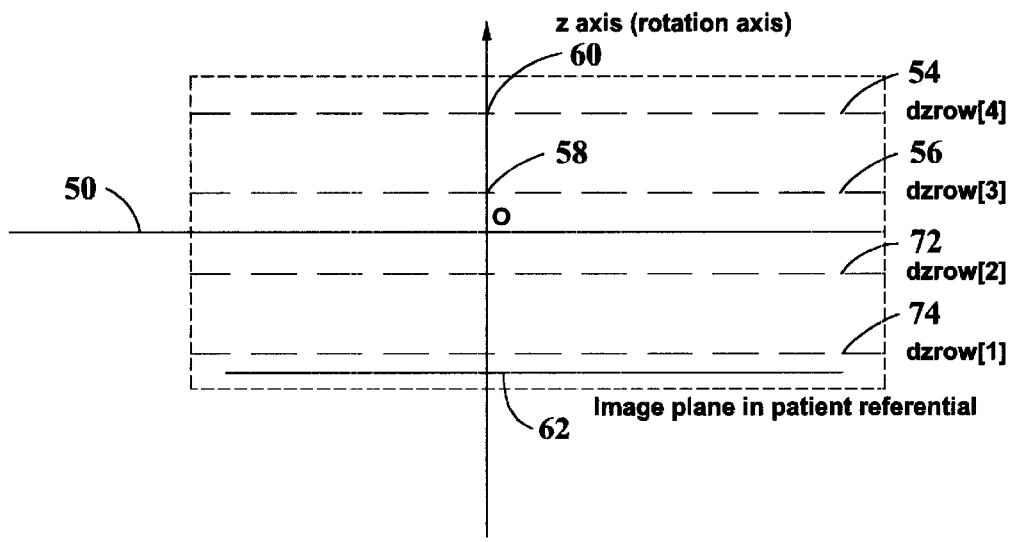
FIG. 7 is a representation of a row-extrapolation condition. This should not be interpreted as meaning that row extrapolation necessarily occurs.

Source positions overlap between $((6-\text{RowO})/7)\pi$ and $((8+\text{RowO})/7)\pi$ (modulo $2\pi$). More specifically, and referring to FIG. 7, for source angles: $((8+\text{RowO})/7)\pi <= \beta <= -\pi$ row 1 is in a row-extrapolation condition. Referring to FIG. 8, source angles $((6-\text{RowO})/7)\pi <= \beta <= \pi$ cover the same range, with row 8 in a row-interpolation condition. In FIGS. 7 and 8, gantry plane 50 intersects the rotation, or z-axis at O, and planes 72 and 74 are planes associated with centers of detector rows 1A and 2A, respectively.

For source angles $-\pi <= \beta <= -((6-\text{RowO})/7)\pi$ row 1 is in the row-interpolation condition. Source angles $\pi <= \beta <= ((8+\text{RowO})/7)\pi$ cover the same range, with row 8 in the row-extrapolation condition.

Increasing values of row-overlap parameter RowO correspond to use of an increasing number of super-views to further abate cone-artifacts. Accordingly, when three measurements of a given line integral are acquired, two measurements at a same end of the line integral are such that one of them is acquired in a row-extrapolation condition, while the other is acquired in a row-interpolation condition.

Row-interpolation/extrapolation does not necessarily occur in all embodiments. For example, a row extrapolation condition can occur only when the line integral is measured from a source 14 position in source overlap region 66. Also, at least one known HQ (high quality) image reconstruction algorithm takes into account conjugate measurements for interpolation/extrapolation. However, it does not take into account transition regions within a fan, as do embodiments of the present invention.

A measurement weighted for contribution to a reconstruction plane is denoted as a direct measurement. At a 7:1 pitch, for every direct measurement there are either one or two other measurements or sets of measurements of the same line integral acquired at different angle of source 14. When there is only one other measurement, the other measurement occurs at a different source angle (modulo $2\pi$) and is denoted as a conjugate measurement. When there are two measurements acquired at different source angles, one of two cases is possible. In a first case, the direct measurement is acquired at a source angle not in the source overlap interval, so that the two conjugate measurements are acquired at source angles equal modulo $2\pi$ and in the overlap region. In a second case, the direct measurement originates from a source angle in the overlap region, so that there exists a conjugate measurement acquired at a source angle not in the overlap region and an alternate direct measurement acquired at the same source angle modulo $2\pi$.

The process of looping over source 14 positions, and for each source position, of looping over detector 18 rows, selects a set of two direct measurement rows that are closest to POR 62. A first of the two measurements is closer to POR 62 and is denoted by DS (direct short). The second of the two measurements is denoted by DL (direct long). Calculations to identify the two direct detector 18 rows closest to POR 62 need only be done once per view. A conjugate source 14 position is then determined, as well as the two detector 18 rows at the conjugate source 14 position that provide the conjugate measurements closest to POR 62. Referring to FIG. 9, these samples are shown as DS, DL, CS, CL, which denote, respectively, direct short, direct long, conjugate short, and conjugate long measurements. If the two conjugate measurements DS and CS are on either side of POR 62, then this sample pair is retained to define a short pair DS, CS, as shown in FIG. 9. In this figure, sloping line L represents a path of a line integral for the conjugate measurement.

Retaining only the short pair leads to streak artifacts due to ray crossovers. Therefore, in one embodiment of the present invention, a long pair of measurements is also used. If both conjugate measurements DS and CS are on the same side of POR 62, then a measurement that is closest to POR 62 is found (either DS or CS) and the other measurements are changed by incrementing the row index by ±1. Thus, in a first case, direct measurement DS is closest to POR 62, while in a second case, conjugate measurement CS is closest to POR 62. In the first case, the conjugate measurement is switched (using conjugate row switching in which CS and CL labels are exchanged) to the measurement at the same (i.e., conjugate) source position, but with the row incremented. As a result, the direct and conjugate positions are on either side of POR 62. In the second case, the direct measurement is switched (using direct row switching in which DS and DL labels are exchanged) such that as a result, the direct and conjugate positions are on either side of POR 62. This row index change is always possible when the conjugate source position is in a range of $[-\pi, \pi]$ with respect to a center view. In this case, it is a row-interpolation condition, and data are acquired with detector rows on either side of POR 62.

Referring to FIG. 10, a pair (DS1, CL1) of measurements is switched for a different pair (DS1, CS2), as the two measurements (DS1, CL1) are on the same side of POR 62. A similar situation occurs if both closest measurements are on the same side of POR 62 (represented by a horizontal line), with the conjugate measurement being closest. In that case, the direct measurement is switched to the alternate direct measurement. Measurement labels are indicated before (top) and after (bottom) switching.

In one embodiment, a loop over source 14 angles is performed to assign helical weights only to direct rays. Conjugate or alternate conjugate measurements are not accessed (nor are helical weights assigned to them, when processing the data from the direct source position), although their sample locations are used in calculating weights for the direct measurement. Each pair of conjugate measurements is assigned a weight in turn, when it is considered as a direct measurement.

As explained above, at a pitch of 7:1 it is always possible to find a pair of conjugate measurements such that both measurements are associated with a row-interpolation condition. Therefore, embodiments of the present invention described above are always able to provide pair selection for any line integral in POR 62 for a 7:1 pitch.

FIG. 11 is a representation of the three pair selection conditions that occur in one embodiment of the present invention at pitches less than 7:1. Case A (samples DLA, DSA, and CSA) is a case with no switching. Case B uses conjugate measurement switching. Case C uses direct measurement switching. Horizontal bold lines 76 represent direct data available at a source 14 position under consideration. Tilted lines 78 represent conjugate rows data. FIG. 10 is drawn to represent a pitch of 7:1 on an imaging system 10 in which detector 18 has eight rows.

On both the direct and conjugate ends of a given line integral, two measurements corresponding to two different rows of detector array 18 are available. These measurements are identified, but not retained, in the embodiment of the present invention described above. It would be tempting to retain as a long pair these two measurements (one direct, DL, one conjugate CL). However, use of these measurements as the "long pair" results in streak artifacts under a wide range of choices for pair blending at a cross-over region in which direct and conjugate sample pairs are at exactly the same z-locations. Thus, in one embodiment of the present invention, the long pair is selected as being given by the two direct measurements the closest to the plane of reconstruction DS and DL measurements. This long pair selection leads to very robust image quality as well as minimum slice broadening as compared to selected aperture, i.e., a thin reconstructed slice. At pitch 7:1 for an eight slice system, such measurements are always available in the source angle range [−π,π]. At the end of the pair selection process, three measurements DS, DL, CS are retained to define two pairs {DS,CS} and {DS,DL}.

As described above, pair selection depends on a comparison between a distance separating two samples for two possible sample pairs. When the distance (δz between the two conjugate rays on the same side of the POR decreases, the two possible measurement pairs sampling locations become increasingly similar; in the limit of (δz–>0, the two pairs sampling locations coincide, as shown in FIG. 8. In such a case, these two pairs are a-priori equally valid sample pairs. Embodiments of the present invention can make an arbitrary selection in this case.

In at least one embodiment, the two pairs are blended when δz is less than a given threshold. Such blending provides better patient dose utilization and noise reduction, smooth transitions from one pair to the next, and cone-angle artifact reduction.

By symmetry, a third pair is defined by {DL,CL}. In at least one embodiment of the present invention, measurements {DS, CS, DL, CS} are retained and combined in three pairs: {DS,CS}, {DS,DL}, and {DL,CL}. Further details of the combination and blending of these pairs are described below.

Although pair selection is always possible at a pitch of 7:1, not all conditions provide 3 available samples. In such a situation one of the two measurements originating in the source overlap angle is in a row-interpolation condition while the other is in a row-extrapolation condition. When data at a given source position are in a row-extrapolation condition, data for an extra row is synthesized. For example, data is extrapolated from to row-to-row to generate an extra row, or: patching of projections is done to provide an extra row of data. Such patching makes use of the fact that, at pitch 7 (or 5), data acquired one rotation earlier (or later) will be at the same z-position.

In one embodiment, to guarantee that data contributions taper to zero at boundaries of an acquisition interval written as ([((8+RowO)/7)π, ((8+RowO)/7)π]), synthesized planar data obtained by helical weighting in source 14 overlap intervals written as ([−((8+RowO)/7)π, −((6−RowO)/7)π] and [((6−RowO)/7)π, ((8+RowO)/7)π] are further multiplied by feathering weights that depend only on source angle. For example, overscan weights such as those written in equations 0.1 or 0.2 are used for feathering. FIG. 12 is a representation of an exemplary feathering for the case RowO=0.0.

Pair selection depends on a comparison between distances separating the two samples for the two possible sample pairs. When the distance between two conjugate rays on the same side of POR 62 decreases, the two possible measurement pairs sampling locations become increasingly similar. In the limit as the distance approaches zero, the two pairs sampling locations are superimposed. In such a case, these two pairs are a-priori equally valid sample pairs, and one embodiment makes an arbitrary selection of one of the two pairs.

Retaining only the short pair leads to streaks at the crossover points where the Short Pair measurements jump from one row to the next. Therefore, in one embodiment, the two pairs are blended when the distance δz is less than a predetermined threshold. Blending provides better patient dose utilization and noise reduction, a smooth transition from one pair to another, and cone-angle artifact reductions.

In one embodiment in which blending is used, BlendW weights Long Pair samples, while CompBlendW weights Short Pair samples. An intermediate variable xxx is written as:

$$xxx = \min(BdSameSide, BdOppositeSide),$$

where:

$$BdSameSide = \left|\frac{dzpC - dzpD}{\Delta z}\right|$$

$$BdOppositeSide = \left|\frac{dzg\_PairS}{\Delta z}\right|$$

and dzpC and dzpD are algebraic distances from CS and DS to POR 62, and dzg_PairS is an algebraic distance between CS and DS samples.

The BlendW calculation of one embodiment of the present invention is described by the following pseudocode:

PairBlendMax=PB, (where PB is a command line parameter); 0<PB<=1.0, with PB close to 0.0 for thin slices and close to 1.0 for thicker SSP.

```
if ((0 < xxx) && (xxx < = DBP × PairBlendMax)) {

BlendW = LPW;          // Long pair contribution when fully blended-in.

} else if (xxx < = PairBlendMax) {

BlendW = LPW × P_feather(1.0 − (xxx − DBP × PairBlendMax)/(PairBlendMax × (1 − DBP)))

} else {

BlendW = .0;

}
``` where P_feather(uu)=uu×uu×(3−2 uu) is a weight blending function such as one of the exemplary blending functions previously described.

In one embodiment utilizing pair blending, the Short Pair contributes most, except near crossover points where the Long Pair contributes more. In the limit as xxx approaches zero, such as when crossover conditions occur, then weights attributed to the short pair samples vanish.

The following pseudo-code represents one embodiment in which the intermediate variable BlendRegW is determnined, and which forces the short pair contribution to 0 at crossover points:

Xxx as above;
NoShortPair is set to NPB (the second command-line parameter; typically set to PB/2.0).
DNPB=0.5;

If (xxx < (DNPB × NoShortPair)) {

}
else if ((xxx > (DNPB × NoShortPair)) && (xxx <= NoShortPair)) {

$$BlendRegW = P\_feather\left(\frac{xxx - (DNPB \times NoShortPair)}{(1.0 - DNPB) \times NoShortPair}\right);$$

}
else if (xxx > = NoShortPair) {

BlendRegW = 1.0;

}

In one embodiment, each helical weight is determined as a function of a distance between the sample and POR 62, and a distance between two samples in the pair under consideration. This procedure yields weights wd and wc (for a short pair), wdL and wcL (for a long pair). These weights can be determined via linear interpolation, for example, or using smoother functions.

In one embodiment, equations written below describe final weight calculations and normalization:

```
        wn=wd+wc;
        Sbw=CompBlendW*BlendRegW;        // This product
determines final short pair contribution
        Lbw=1.0-Sbw;                      // From which the
final long pair contribution derives.
        wd*=Sbw/wn;
        wc*=Sbw/wn;
        wn=wdL+wcL;
        wdL*=Lbw/wn;
        wcL*=Lbw/wn;
        wn=2.0*Lbw+Sbw;
        wd/=wn;
    wc/=wn;
    wdL/=wn;
    wcL/ =wn;
```

In each case, PB>NPB. A default choice could be NPB= PB/2.0, for example.

In case the 3-pairs option has been retained, three-pair blending proceeds as follows, in one embodiment:
dzpCL3=dzpCL;
dzpCL=dzpD;

In one embodiment, regularization calculations are performed. These calculations are performed using equations and pseudocode written as::

$$vvv1 = \left|\frac{dzpC}{\Delta z}\right|;$$

-continued $$vvv2 = \left|\frac{dzpD}{\Delta z}\right|;$$

uuu=min(vvv1,vvv2);

if (uuu < (DNPB × NoShortPair) {

BlendRegW3 = 0.0;

} else if ((uuu > = (DNPB × NoShortPair)) && (uuu

< = NoShortPair))) {

$$BlendRegW3 = P\_feather\left(\frac{uuu - DNBP \times NoShortPair}{(1 - DNPB) \times NoShortPair}\right)$$

}
else if (uuu > NoShortPair) {

BlendRegW3 = 1.0;

}

Final weight calculations and normalization are performed. In one embodiment, the final weight calculations and normnalizations are described by the following pseudocode:

```
    L3c=L3c0;                            //Third pair contribution
when fully blended in.
    L3c*BlendRegW3;                      //Third pair
contribution after 3rd pair regularization
    Sc=1.0-L3c;                          //Initial Short Pair
contribution
    Sbw=Sc*CompBlendW*BlendRegW;         //Regularized Short
Pair contribution
    L3bw=L3c*CompBlendW*BlendRegW;       //Regularized third
pair contribution
    Lbw=1.0-(Sbw+L3bw);                  // Regularized Long
Pair contribution
    wn=wd+wc;
    wd*=Sbw/wn;
    Wc*=Sbw/wn;
    wn=wdL+wcL;
    wdL*=Lbw/wn;
    wcL*=Lbw/wn;
    wn=wdL3+wcL3                         //Third pair helical weight
normalization coefficient
wn=2.0Lbw*Sbw+L3bw;                      //Helical weight normalization
    wd/=wn;
wc/=wn;
wdL/=wn;
wcL/=wn;
wdL3/=wn;                                //Final third pair helical
weights
wcL3/=wn;
```

The most straightforward helical weighting functions are derived from linear interpolation/extrapolation expressions. However, the linear model introduces discontinuities in the first derivative of the weights, which may result in streak artifacts when POR 62 crosses from one row into a next row. The risk of streak artifacts is reduced in one embodiment by z-smoothing, and further alleviated by the use of smoother helical weighting functions. Examples of such functions are shown in FIGS. 13, 14, and 15.

For example and referring to FIG. 13, in one embodiment, an apodized sinc( ) weight function is used. The negative lobe is feathered to zero. Note that in general $\Delta z_1 \neq \Delta z_2$, where $\Delta z$'s represent the intervals between samples.

In another embodiment and referring to FIG. 14, SHE1 helical weightings are used:

$$hw(x) = \frac{NN}{DD}$$

$$NN = \left|\sin\left(\pi\frac{1-x}{2}\right)\right|^6$$

$$DD = NN + \left|\cos\left(\pi\frac{1-x}{2}\right)\right|^6$$

In yet another embodiment and referring to FIG. 15, SHE2 helical weightings are used:

$$hw(x) = \sin^2\left(\pi\frac{1-x}{2}\right)$$

In one embodiment, a feathering function $3x^2-2x^3$ is applied.

Variable reconstructed image thickness is provided in one embodiment by changing an "x" factor in a z-smoothing approach, where the terminology "x-factor" refers to a slice broadening. Thus, x=1.2 represents a 20% slice broadening, x=2 represents a doubling of the slice thickness, etc. By broadening the slice profile, z-smoothing reduces helical artifacts and allows tube current reduction. In discrete form, the z-smoothing equation is written as:

$$W_{ZS}(\beta, \gamma) = \sum_{i=1}^{T} h(i) \times W(\beta - i \times \Delta\beta, \gamma)$$

where h represents the z-smoothing kernel (such as {1/3,1/3,1/3}), T is the number of terms (for example, 3 in the previous example), and $\Delta\beta$ is the view increment between each of the image planes contributing through z-smoothing to the final reconstructed image.

The slice sensitivity profile generated by one known fast high-quality reconstruction algorithm (HQ Fast) presents a slice broadening by a factor of approximately 1.33. As that algorithm uses only row-to-row interpolation without consideration of conjugate rays, it is simple and fast to execute. As the pitches retained for the HQ-Fast algorithm cover the HQ pitches, it is inefficient to use the HQ algorithm with a z-smoothing factor leading to a slice broadening factor greater than 1.3.

In the overlap region, some embodiments of the present invention use a method selected from extrapolation and fetching of matching data from a previous/following rotation for synthesizing data for two extra rows. These methods ensure that similar processing steps are used throughout the range of processed views.

In one embodiment, the new parameter pair (PB, NPB) is used in a manner in which NPB<PB is always true. NPB= 0.5×PB can be used as a default.

Small values of PB correspond to limited use of the long-pair for regularization weighting. With PB values smaller than about 0.04, artifacts start to appear in one known imaging system 10 in 4-row mode with pitch 3:1 images. With PB values smaller than about 0.1, artifacts start to appear in a second known imaging system in 8-row mode with pitch 7:1 images. Larger values of PB increase the contribution of the Long Pair. In the limit, with the appropriate default values for LPW (LPW=1.0), the HQ algorithm reduces to the HQ-F algorithm.

A number of superviews (i.e., data acquired at a given source position) is given as a function of a z-smoothing factor parameter zsf written as:

$$N\_Superviews = (N\_views\_2\pi) \times \left(\frac{Nrows + RowO + (zsf - 1.0)}{Pitch}\right).$$

The slice broadening is not given directly by the zsf parameter. However, a one-to-one correspondence between slice broadening and zsf exists for which the slice-broadening parameter is always less than the zsf parameter. This correspondence is determined empirically for various scan data acquisition techniques and parameters settings via experiments and ensuing regressions.

To summarize, in one embodiment, the present invention provides a method for imaging an object utilizing a computed tomographic (CT) imaging system. The CT imaging system includes a radiation source and a multislice detector array on a rotating gantry, the radiation source configured to project a fan-shaped beam of radiation through an object to be imaged towards the detector array, and the detector array having a plurality of detector elements configured to produce electrical signals indicative of attenuation of the beam of radiation passing through the object. The CT imaging system also has a z-axis defined by an axis of rotation of the gantry. In one embodiment, the method includes steps of scanning an object at a selected helical pitch with a CT imaging system to acquire a set of attenuation measurements of the object; for each angle of the fan beam of radiation corresponding to a detector element of the detector array, identifying a direct set of attenuation measurements and a conjugate set of attenuation measurements, each said set of measurements comprising at least two measurements closest to a plane of reconstruction, the direct set of attenuation measurements being measurements that are acquired at a source angle $\beta$ and a fan angle $\gamma$ and the conjugate set being measurements that are acquired at a source angle of either $\beta+\pi+2\gamma$ or $\beta-\pi+2\gamma$ and a fan angle $-\gamma$; arranging the measurements of the identified sets of measurements in pairs, including at least one short pair comprising a direct measurement and a conjugate measurement that are closest to the plane of reconstruction and on opposite sides of the plane of reconstruction, and one long pair comprising two direct measurements on opposite sides of the plane of reconstruction; weighting the direct measurements in accordance with their distance from the plane of reconstruction, wherein the weights of the short pair and the long pair are each normalized; blending the direct measurements of the short pair and the long pair in accordance with a blending function such that at a point at which the selected direct pair and the selected conjugate pair have a same z-axis location, the short pair contribution to the blend is weighted to zero, and the contribution increases at a distance further from the z-axis location; and filtering and backprojecting the weighted and blended data to reconstruct the image of the object.

In one embodiment, the method utilizes CT imaging system having a multislice detector array with N rows, and the selected helical pitch is one of either N−1 or N−3. In another embodiment, the step of weighting the direct measurements comprises determining a helical weight as a function of a distance between the direct measurements and the plane of reconstruction, and a distance between the two measurements in each pair. Also in one embodiment, the step of determining a helical weight comprises the step of determining a helical weight utilizing linear interpolation/extrapolation expressions. In yet another embodiment, blending the direct measurements of the short pair and the long pair comprises the step of utlizing a blending function that is dependent upon a distance between the conjugate measurement retained in the short pair and a direct measurement closest to the conjugate measurement retained in the short pair.

Another embodiment of the present invention utilizes three pairs of points. In this embodiment, the method includes steps of: scanning an object at a selected helical pitch with a CT imaging system to acquire a set of attenuation measurements of the object; for each angle of the fan beam of radiation corresponding to a detector element of the detector array, identifying a direct set of attenuation measurements and a conjugate set of attenuation measurements, each said set of measurements comprising at least two measurements closest to a plane of reconstruction, the direct set of attenuation measurements being measurements that are acquired at a source angle $\beta$ and a fan angle $\gamma$ and the conjugate set being measurements that are acquired at a source angle of either $\beta+\pi+2\gamma$ or $\beta-\pi+2\gamma$ and a fan angle $-\gamma$; arranging the measurements of the identified sets of measurements in pairs, including at least one short pair comprising a direct measurement and a conjugate measurement that are closest to the plane of reconstruction and on opposite sides of the plane of reconstruction, a one long pair comprising two direct measurements on opposite sides of the plane of reconstruction, and a third pair comprising a conjugate measurement other than the conjugate measurement retained in the short pair and a direct measurement not retained in the short pair; weighting the direct measurements in accordance with their distance from the plane of reconstruction, wherein the weights of the short pair, the long pair, and the third pair are each normalized; blending the direct measurements of the short pair, the long pair, and the third pair in accordance with a blending function such that at a point at which the selected direct pair and the selected conjugate pair have a same z-axis location, the short pair contribution to the blend is weighted to zero, and the contribution increases at a distance further from the z-axis location; and filtering and backprojecting the weighted and blended data to reconstruct the image of the object.

In one embodiment of the present invention, imaging system 10 is configured to carry out the method steps. Thus, in one exemplary embodiment, image reconstructor 34 is configured using software or firmware to carry out the method steps.

It will be observed that the various embodiments of the present invention provide thin slice sensitivity profiles from acquired data at a fairly high pitch, without deconvolution. Moreover, the methods and apparatus embodiments of the present invention can be applied to CT imaging systems with various numbers of detector rows, and at multiple pitches.

While the invention has been described in terms of various specific embodiments, those skilled in the art will recognize that the invention can be practiced with modification within the spirit and scope of the claims.

What is claimed is:

1. A method for imaging an object utilizing a computed tomographic (CT) imaging system, the CT imaging system having a radiation source and a multislice detector array on a rotating gantry, the radiation source configured to project a fan-shaped beam of radiation through an object to be imaged towards the detector array, and the detector array having a plurality of detector elements configured to produce electrical signals indicative of attenuation of the beam of radiation passing through the object, the CT imaging system also having a z-axis defined by an axis of rotation of the gantry, said method comprising the steps of:

scanning an object at a selected helical pitch with a CT imaging system to acquire a set of attenuation measurements of the object;

for each angle of the fan beam of radiation corresponding to a detector element of the detector array, identifying a direct set of attenuation measurements and a conjugate set of attenuation measurements, each said set of measurements comprising at least two measurements closest to a plane of reconstruction, the direct set of attenuation measurements being measurements that are acquired at a source angle $\beta$ and a fan angle $\gamma$ and the conjugate set being measurements that are acquired at a source angle of either $\beta+\pi+2\gamma$ or $\beta-\pi+2\gamma$ and a fan angle $-\gamma$;

arranging the measurements of the identified sets of measurements in pairs, including at least one short pair comprising a direct measurement and a conjugate measurement that are closest to the plane of reconstruction and on opposite sides of the plane of reconstruction, and one long pair comprising two direct measurements on opposite sides of the plane of reconstruction;

weighting the direct measurements in accordance with their distance from the plane of reconstruction, wherein the weights of the short pair and the long pair are each normalized;

blending the direct measurements of the short pair and the long pair in accordance with a blending function such that at a point at which the selected direct pair and the selected conjugate pair have a same z-axis location, the short pair contribution to the blend is weighted to zero, and the contribution increases at a distance further from the z-axis location; and filtering and backprojecting the weighted and blended data to reconstruct the image of the object.

2. A method in accordance with claim 1 wherein the multislice detector array has N rows, and the selected helical pitch is one of either N−1 or N−3.

3. A method in accordance with claim 1 wherein the step of weighting the direct measurements comprises determining a helical weight as a function of a distance between the direct measurements and the plane of reconstruction, and a distance between the two measurements in each pair.

4. A method in accordance with claim 3 wherein said step of determining a helical weight comprises the step of determining a helical weight utilizing linear interpolation/extrapolation expressions.

5. A method in accordance with claim 1 wherein blending the direct measurements of the short pair and the long pair comprises the step of utilizing a blending function that is dependent upon a distance between the conjugate measurement retained in the short pair and a direct measurement closest to the conjugate measurement retained in the short pair.

6. A method for imaging an object utilizing a computed tomographic (CT) imaging system, the CT imaging system having a radiation source and a multislice detector array on a rotating gantry, the radiation source configured to project a fan-shaped beam of radiation through an object to be imaged towards the detector array, and the detector array having a plurality of detector elements configured to produce electrical signals indicative of attenuation of the beam of radiation passing through the object, the CT imaging system also having a z-axis defined by an axis of rotation of the gantry, said method comprising the steps of:

scanning an object at a selected helical pitch with a CT imaging system to acquire a set of attenuation measurements of the object;

for each angle of the fan beam of radiation corresponding to a detector element of the detector array, identifying a direct set of attenuation measurements and a conjugate set of attenuation measurements, each said set of measurements comprising at least two measurements closest to a plane of reconstruction, the direct set of attenuation measurements being measurements that are acquired at a source angle $\beta$ and a fan angle $\gamma$ and the conjugate set being measurements that are acquired at a source angle of either $\beta+\pi+2\gamma$ or $\beta-\pi+2\gamma$ and a fan angle $-\gamma$;

arranging the measurements of the identified sets of measurements in pairs, including at least one short pair comprising a direct measurement and a conjugate measurement that are closest to the plane of reconstruction and on opposite sides of the plane of reconstruction, one long pair comprising two direct measurements on opposite sides of the plane of reconstruction, and a third pair comprising a conjugate measurement other than the conjugate measurement retained in the short pair and a direct measurement not retained in the short pair;

weighting the direct measurements in accordance with their distance from the plane of reconstruction, wherein the weights of the short pair, the long pair, and the third pair are each normalized;

blending the direct measurements of the short pair, the long pair, and the third pair in accordance with a blending function such that at a point at which the selected direct pair and the selected conjugate pair have a same z-axis location, the short pair contribution to the blend is weighted to zero, and the contribution increases at a distance further from the z-axis location; and filtering and backprojecting the weighted and blended data to reconstruct the image of the object.

7. A method in accordance with claim 6 wherein the multislice detector array has N rows, and the selected helical pitch is one of either N-1 or N-3.

8. A method in accordance with claim 6 wherein the step of weighting the direct measurements comprises determining a helical weight as a function of a distance between the direct measurements and the plane of reconstruction, and a distance between the two measurements in each pair.

9. A method in accordance with claim 8 wherein said step of determining a helical weight comprises the step of determining a helical weight utilizing linear interpolation/extrapolation expressions.

10. A computed tomographic (CT) imaging system for imaging an object, said CT imaging system comprising a radiation source and a multislice detector array on a rotating gantry, the radiation source configured to project a fan-shaped beam of radiation through an object to be imaged towards the detector array, and the detector array having a plurality of detector elements configured to produce electrical signals indicative of attenuation of the beam of radiation passing through the object, the CT imaging system also having a z-axis defined by an axis of rotation of the gantry, said CT imaging system configured to:

scan an object at a selected helical pitch with a CT imaging system to acquire a set of attenuation measurements of the object;

for each angle of the fan beam of radiation corresponding to a detector element of the detector array, identify a direct set of attenuation measurements and a conjugate set of attenuation measurements, each said set of measurements comprising at least two measurements closest to a plane of reconstruction, the direct set of attenuation measurements being measurements that are acquired at a source angle $\beta$ and a fan angle $\gamma$ and the conjugate set being measurements that are acquired at a source angle of either $\beta+\pi+2\gamma$ or $\beta-\pi+2\gamma$ and a fan angle $-\gamma$;

arrange the measurements of the identified sets of measurements in pairs, including at least one short pair comprising a direct measurement and a conjugate measurement that are closest to the plane of reconstruction and on opposite sides of the plane of reconstruction, and one long pair comprising two direct measurements on opposite sides of the plane of reconstruction;

weight the direct measurements in accordance with their distance from the plane of reconstruction, wherein the weights of the short pair and the long pair are each normalized;

blend the direct measurements of the short pair and the long pair in accordance with a blending function such that at a point at which the selected direct pair and the selected conjugate pair have a same z-axis location, the short pair contribution to the blend is weighted to zero, and the contribution increases at a distance further from the z-axis location; and filter and backproject the weighted and blended data to reconstruct the image of the object.

11. A CT imaging system in accordance with claim 10 wherein the multislice detector array has N rows, and wherein said CT imaging system is configured to scan at a selected helical pitch including a helical pitch selected from N-1 and N-3.

12. A CT imaging system in accordance with claim 10 wherein to weight the direct measurements, said CT imaging system is configured to determine a helical weight as a function of a distance between the direct measurements and the plane of reconstruction, and a distance between the two measurements in each pair.

13. A CT imaging system in accordance with claim 12 wherein to determine a helical weight, said CT imaging system is configured to utilize linear interpolation/extrapolation expressions.

14. A CT imaging system in accordance with claim 10 wherein to blend the direct measurements of the short pair and the long pair, said CT imaging system is configured to utilize a blending function that is dependent upon a distance between the conjugate measurement retained in the short pair and a direct measurement closest to the conjugate measurement retained in the short pair.

15. A computed tomographic (CT) imaging system for imaging an object, said CT imaging system comprising a radiation source and a multislice detector array on a rotating gantry, the radiation source configured to project a fan-shaped beam of radiation through an object to be imaged towards the detector array, and the detector array having a plurality of detector elements configured to produce electrical signals indicative of attenuation of the beam of radiation passing through the object, the CT imaging system also having a z-axis defined by an axis of rotation of the gantry, said CT imaging system configured to:

scan an object at a selected helical pitch with a CT imaging system to acquire a set of attenuation measurements of the object;

for each angle of the fan beam of radiation corresponding to a detector element of the detector array, identify a direct set of attenuation measurements and a conjugate set of attenuation measurements, each said set of measurements comprising at least two measurements closest to a plane of reconstruction, the direct set of attenuation measurements being measurements that are acquired at a source angle $\beta$ and a fan angle $\gamma$ and the conjugate set being measurements that are acquired at a source angle of either $\beta+\pi+2\gamma$ or $\beta-\pi+2\gamma$ and a fan angle $-\gamma$;

arrange the measurements of the identified sets of measurements in pairs, including at least one short pair comprising a direct measurement and a conjugate measurement that are closest to the plane of reconstruction and on opposite sides of the plane of reconstruction, one long pair comprising two direct measurements on opposite sides of the plane of reconstruction, and a third pair comprising a conjugate measurement other than the conjugate measurement retained in the short pair and a direct measurement not retained in the short pair;

weight the direct measurements in accordance with their distance from the plane of reconstruction, wherein the weights of the short pair, the long pair, and the third pair are each normalized;

blend the direct measurements of the short pair, the long pair, and the third pair in accordance with a blending function such that at a point at which the selected direct pair and the selected conjugate pair have a same z-axis location, the short pair contribution to the blend is weighted to zero, and the contribution increases at a distance further from the z-axis location; and filter and backproject the weighted and blended data to reconstruct the image of the object.

16. A CT imaging system in accordance with claim 15 wherein the multislice detector array has N rows, and wherein said CT imaging system is configured to scan at a selected helical pitch including a helical pitch selected from N−1 and N−3.

17. A CT imaging system in accordance with claim 15 wherein to weight said direct measurements, said CT imaging system is configured to determine a helical weight as a function of a distance between the direct measurements and the plane of reconstruction, and a distance between the two measurements in each pair.

18. A CT imaging system in accordance with claim 17 wherein to determine a helical weight, said CT imaging system is configured to utilize linear interpolation/extrapolation expressions.

\* \* \* \* \*

UNITED STATES PATENT AND TRADEMARK OFFICE
CERTIFICATE OF CORRECTION

PATENT NO.    : 6,463,118 B2
DATED         : October 8, 2002
INVENTOR(S)   : Besson It is certified that error appears in the above-identified patent and that said Letters Patent is hereby corrected as shown below:

<u>Title page, Item [54] and Column 1, line 3,</u>
Title, delete "RECONTRUCTION" and insert therefor
-- RECONSTRUCTION --.

Signed and Sealed this

Twenty-fifth Day of February, 2003

JAMES E. ROGAN
*Director of the United States Patent and Trademark Office*